(12) United States Patent
Pechstein et al.

(10) Patent No.: US 7,799,606 B2
(45) Date of Patent: Sep. 21, 2010

(54) SEMICONDUCTOR SENSOR HAVING A FRONT-SIDE CONTACT ZONE

(75) Inventors: Torsten Pechstein, Radebeul (DE); Robert Scholz, Lüttewitz/Döbeln (DE)

(73) Assignee: Endress + Hauser Conducta Gesellschaft fur Mess- u. Regeltechnik mbH + Co. KG (DE)

( * ) Notice: Subject to any disclaimer, the term of this patent is extended or adjusted under 35 U.S.C. 154(b) by 1168 days.

(21) Appl. No.: 10/539,799

(22) PCT Filed: Dec. 6, 2003

(86) PCT No.: PCT/EP03/13839
§ 371 (c)(1),
(2), (4) Date: Feb. 6, 2006

(87) PCT Pub. No.: WO2004/059311
PCT Pub. Date: Jul. 15, 2004

(65) Prior Publication Data
US 2006/0159590 A1 Jul. 20, 2006

(30) Foreign Application Priority Data
Dec. 20, 2002 (DE) ................... 102 60 961

(51) Int. Cl.
*H01L 21/00* (2006.01)
*G01N 27/26* (2006.01)
*G01N 21/00* (2006.01)

(52) U.S. Cl. ............. 438/108; 422/82; 422/88; 438/48; 438/49; 438/456; 204/416; 204/433; 257/253

(58) Field of Classification Search ............. 422/82, 422/88; 438/48, 49, 108, 456; 204/416, 204/433; 257/253
See application file for complete search history.

(56) References Cited

U.S. PATENT DOCUMENTS

| | | | | |
|---|---|---|---|---|
| 5,393,401 A | * | 2/1995 | Knoll | 204/403.06 |
| 5,414,284 A | * | 5/1995 | Baxter et al. | 257/253 |
| 5,521,123 A | * | 5/1996 | Komatsu et al. | 438/64 |
| 5,833,824 A | | 11/1998 | Benton | |

(Continued)

FOREIGN PATENT DOCUMENTS

DE  690 13 056 T2  5/1995

(Continued)

*Primary Examiner*—Jill Warden
*Assistant Examiner*—Dean Kwak
(74) *Attorney, Agent, or Firm*—Bacon & Thomas, PLLC

(57) ABSTRACT

An ion-sensitive sensor arrangement includes: a semiconductor chip having a first surface, which has a media-sensitive region and at least one, first, electrical contact surface; and a support having a second surface, which faces the first surface of the semiconductor chip. An opening is provided, which aligns with the sensitive region, and at least one, second, electrical contact surface, which overlaps, or aligns with, the at least one, first, electrical contact surface. Between the support and the semiconductor chip, a preferably elastic, anisotropic conductor is arranged, which produces a conducting connection between the at least one, first, contact surface and the at least one, second, contact surface, and which has a traversing opening, which aligns with the opening, so that the sensitive region of the semiconductor chip can be contacted through the opening by an analyte. The preferably elastic, anisotropic conductor seals the region outside of the opening against contamination with the analyte.

6 Claims, 1 Drawing Sheet

U.S. PATENT DOCUMENTS

| | | | |
|---|---|---|---|
| 5,858,862 A * | 1/1999 | Westwater et al. | 438/503 |
| 6,140,144 A * | 10/2000 | Najafi et al. | 438/53 |
| 6,153,070 A | 11/2000 | Maurer | |
| 6,340,894 B1 * | 1/2002 | Farnworth et al. | 324/755 |
| 6,396,712 B1 | 5/2002 | Kuijk | |
| 6,579,106 B1 * | 6/2003 | Cheng et al. | 439/66 |
| 2004/0056673 A1 * | 3/2004 | Cram | 324/754 |

FOREIGN PATENT DOCUMENTS

| | | |
|---|---|---|
| DE | 694 08 558 T2 | 7/1998 |
| DE | 198 34 396 A1 | 2/2000 |
| DE | 198 46 232 A1 | 3/2000 |
| JP | 2-223855 | 9/1990 |

* cited by examiner

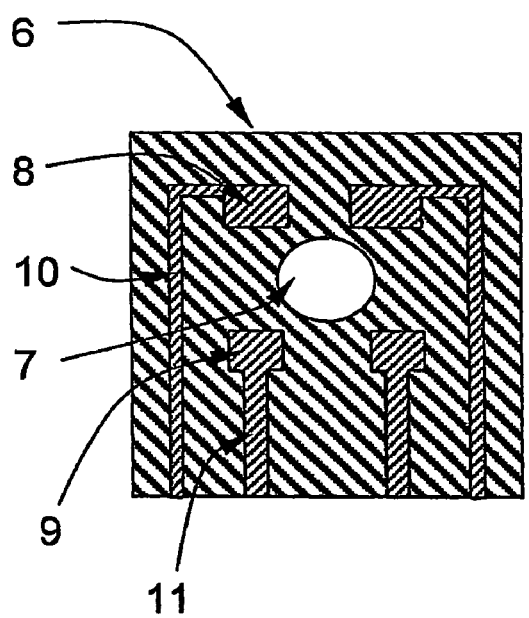
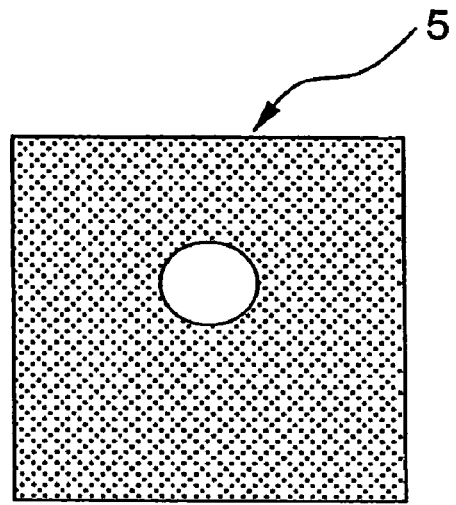
Fig. 1    Fig. 2
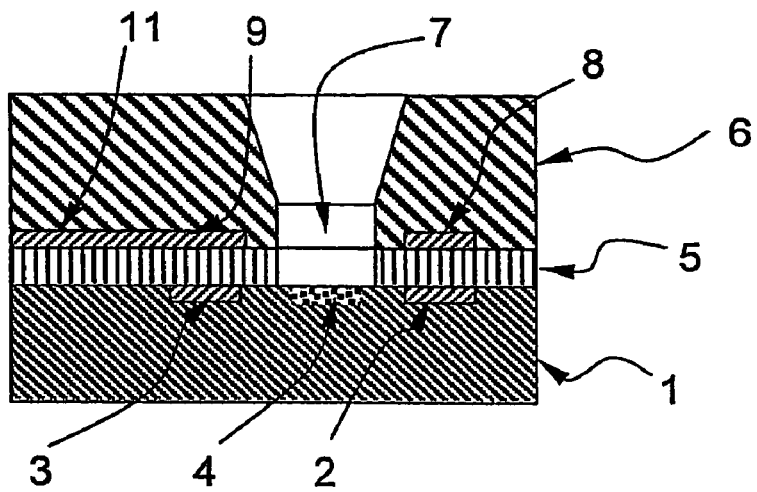
Fig. 3

SEMICONDUCTOR SENSOR HAVING A FRONT-SIDE CONTACT ZONE

FIELD OF THE INVENTION

The present invention concerns a semiconductor sensor, especially a so-called ISFET or CHEMFET sensor, which includes an ion-sensitive, field effect transistor.

BACKGROUND OF THE INVENTION

The ion-sensitive elements, which are present in the form of chips, must, in order to realize their purpose, be mounted such that they can, on the one hand, be subjected to the usually highly corrosive samples, without that, on the other hand, corrosion-susceptible components, such as conductive traces, come in contact with the media. To this end, the ion-sensitive element of a semiconductor chip is usually arranged aligned with an opening in a wall of a sample chamber, with an annular seal being arranged between the wall of the sample chamber and the semiconductor chip. The annular seal surrounds the opening, so that the ion-sensitive region of the semiconductor chip can be subjected to the sample, without the sample being able to reach the areas of the chip outside of the ion sensitive region.

The electric contacting of the chip proves, however, to be difficult. The state of the art uses essentially three approaches. Benton discloses in U.S. Pat. No. 5,833,824 a pH-sensor, in which an ISFET chip is secured on the underside of a substrate by means of a metal seal, which surrounds the ion-sensitive region of the ISFET chip, with the ion-sensitive region being aligned with an opening in the substrate. Outside of the region surrounded by the seal, conductive traces on the surface of the chip extend to contact surfaces, which are connected via solder or weld connections with complementary contact surfaces on the underside of the substrate. The solution proposed by Benton is very expensive in the respect that both during the manufacture of the seal and also during the effecting of the electrical contacting, expensive soldering and/or welding processes are required.

The state of the art discussed in Benton describes ISFET sensors, in which an ordinary polymeric seal is arranged about the opening of the sample chamber wall between the substrate and the ion-sensitive region of the ISFET chip. The contacting of the ISFET chip occurs, however, not to the substrate, in the sense of Benton, but, instead, to a support, which supports the ISFET chip on the rear side facing away from the substrate. To this end, bond wires are extended between contact surfaces on the front side of the ISFET chip to contact surfaces on the support outside of the bearing surface of the ISFET chip. Even this solution is expensive, because solder work is required for contacting the chip and because, in order to assure the functioning and integrity of the sensor, the chip must be placed within narrow tolerances with respect both to the substrate and the support.

Additionally, solutions are known, in which the chips have their contact surfaces, or bond pads, on the rear side facing away from the ion-sensitive region. These chips can then be contacted on the rear side via a support having complementary contact surfaces, wherein, for assuring sufficient, galvanic contacts between the rear side of the chip and the support, an anisotropic, elastic conductor, e.g. a silicone film with embedded gold filaments, is arranged in a direction perpendicular to the plane of the film.

This solution is very costly with respect to leading of the electrical contacts through the chip from its front side to its rear side increases its manufacturing costs several times.

SUMMARY OF THE INVENTION

It is, therefore, an object of the present invention to provide a semiconductor sensor that overcomes the described disadvantages. The object is achieved according to the invention by the sensor of the independent claim 1.

The sensor of the invention includes: A semiconductor chip having a first surface, which has a media-sensitive region and at least one, first, electrical contact surface; and a support having a second surface, which faces the first surface of the semiconductor chip, has an opening aligned with the sensitive region, and at least one, second, electrical contact surface, which overlaps, or aligns, with the at least one, first, electrical contact surface; wherein, between the support and the semiconductor chip, a preferably elastic, anisotropic conductor is arranged, which produces a conducting connection between the at least one, first, contact surface and the at least one, second, contact surface; wherein the film or layer has a traversing opening aligned with the opening in the second surface, so that the sensitive region of the semiconductor chip can be contacted through the opening with an analyte; wherein the preferably elastic, anisotropic conductor seals the region outside of the opening against contamination with the analyte.

Preferably, the anisotropic conductor comprises an elastic, insulating, organic layer with embedded, conductive particles, grains or filaments, especially metal particles, or filaments. Especially preferred at this time are gold filaments, which extend perpendicularly to the plane of the elastic, organic layer. Especially preferred at this time are silicone layers, which have gold filaments and are available commercially from the firm Shin-Etsu.

To the extent that the organic, elastic layer has metal grains, these are, in a relaxed state of the layer, uniformly distributed in the layer in a concentration such that there are insufficient electrical contacts between grains to produce an electrical conductivity over large distances. If, however, the elastic layer is compressed in one direction, for example from clamping when serving as a sealing element, then a sufficient number of electrical contacts arise in the direction of compression that conductivity in the direction of compression is assured.

Independently of the selected type of sealing element, the semiconductor chip is preferably pressed by a rear-side support against the elastic layer, in order to optimize the sealing action of the elastic layer. The rear-side support can be both stiff and elastically prestressed. The elastic prestress, e.g. by way of a coil spring, is advantageous in that the effects of differing coefficients of thermal expansion can be accommodated better, compared with when this must occur solely on the basis of the elasticity of the sealing element. This is especially important, when a certain degree of compression of the sealing element is required, in order to assure the electrical conductivity through the seal.

BRIEF DESCRIPTION OF THE DRAWINGS

Further details will become apparent from the accompanying drawings, the figures of which show as follows:

FIG. 1 a plan view onto the underside of a substrate for a semiconductor sensor of the invention;

FIG. 2 a sealing element for a semiconductor sensor of the invention; and

FIG. 3 a longitudinal section through a semiconductor sensor of the invention.

DESCRIPTION OF THE PREFERRED EMBODIMENT

FIG. 1 shows the underside of a substrate for a semiconductor sensor of the invention. Contact surfaces 8, 9 are arranged on the underside, spaced from an opening 7. Contact surfaces 8, 9 are connected via conductive traces 10, 11 with junctions as required. In completed assembly of the sensor, opening 7 serves to permit contacting of the semiconductor chip with sample to be analyzed.

FIG. 2 shows a plan view of a sealing element 5 for the semiconductor sensor of the present invention, with the sealing element of this embodiment comprising a silicone layer, which contains traversing gold filaments, which extend essentially perpendicular to the plane of the sealing element. In this way, the sealing element is insulating in the plane of the sealing element and conductive perpendicular to the plane of the sealing element. Consequently, mutually aligned, electric contact surfaces mutually separated by the seal, can nevertheless be in electrical contact with one another, while contact surfaces laterally displaced from one another in the plane of the sealing element are electrically insulated from one another.

The required minimum size of aligned contact surfaces for assuring a safe contact is a question of the average number of gold filaments per unit surface area of the sealing element. This parameter can be coordinated in suitable manner by those skilled in the art. In the same way, the average lateral separation of components for assuring a reliable insulating is a function of the number density of gold filaments, as well as their orientation and their diameter. Presently, a sealing element is preferred, which enables a reliable contacting of aligned contact surfaces of some few square millimeters and a sufficient insulation at a lateral separation of about 1 millimeter.

The outer dimensions of the sealing element of FIG. 2 are congruent in this form of embodiment with the outer dimensions of the underside of the substrate in FIG. 1; this is, however, not compulsory. It is expedient, however, that the opening in the sealing element has about the same size as the opening 7 in the underside of the substrate 6.

FIG. 3 shows a longitudinal section through the assembled semiconductor sensor of the present invention, wherein the sealing element 5 is clamped between a semiconductor chip 1 and the substrate 6.

The semiconductor chip 1 has, in its surface facing the sealing element, an ion-sensitive region 4, which aligns with the opening 7 of substrate 6. Spaced from the opening are contact surfaces 2 and 3, which align with the complementary contact surfaces 8, 9 on the underside of the substrate. The contacting between the chip-side contact surfaces 2, 3 and the substrate-side contact surfaces 8, 9 is assured by the conductivity of the sealing element perpendicular to its plane.

In order to achieve a sufficient sealing, the semiconductor chip 1 must be pressed with sufficient force against the underside of the substrate 6. This can, on the one hand, occur by a clamping with dimensionally stable structural elements (not shown), and, on the other hand, by elastic elements, such as e.g. a coil spring (not shown).

The substrate 6 can be formed e.g. as one piece with a housing of a semiconductor sensor or as a separate component, which is installed in suitable manner into a housing. These and similar embodiments will be apparent to those skilled in the art on the basis of what has been described above and lie within the scope of the invention, as such is defined in the patent claims below.

The invention claimed is:

1. A sensor arrangement, comprising:
    a semiconductor chip having a first surface, which has a media-sensitive region and at least one, first, electrical contact surface;
    a support having a second surface, which faces said first surface of said semiconductor chip, has an opening, which at least overlaps with said media-sensitive region, and at least one, second, electrical contact surface, which at least overlaps with said at least one, first, electrical contact surface; and
    a sealing element, which is clamped between said support and said semiconductor chip and produces an electrically conducting connection between said at least one, first, contact surface and said at least one, second, contact surface, and which has a traversing opening, which at least overlaps with the opening in said second surface, so that said media-sensitive region of said semiconductor opening is contactable through said opening with an analyte, wherein:
    said sealing element is elastic and seals the region outside of said opening against contamination with the analyte;
    said elastic sealing element comprises an elastic, insulating, organic layer with a plurality of embedded, conductive particles, grains or filaments; and
    said semiconductor chip is a pH sensor element or a redox sensor element.

2. The sensor arrangement as claimed in claim 1, wherein:
    said elastic, sealing element comprises a silicone layer with embedded gold filaments, which extend perpendicular to the plane of the silicone layer.

3. The sensor arrangement as claimed in claim 1, wherein:
    said elastic insulating organic layer includes embedded, metal grains in the relaxed state in a concentration such that the number of electrical contacts between the grains is insufficient to produce a continuous electrical conductivity; and
    by clamping of said elastic insulating organic layer as a sealing element between said support and said semiconductor chip, said elastic insulating organic layer is compressed to a degree such that, in the direction of compression, a sufficient number of electrical contacts is present for producing a conducting connection between said at least one, first, contact surface and said at least one, second, contact surface.

4. The sensor arrangement as claimed in claim 1, wherein:
    said semiconductor chip has an ion-sensitive region.

5. A sensor arrangement comprising:
    a semiconductor chip having a first surface, which has a media-sensitive region and at least one, first, electrical contact surface;
    a support having a second surface, which faces said first surface of said semiconductor chip, has an opening, which at least overlaps with said media-sensitive region, and at least one, second, electrical contact surface, which at least overlaps with said at least one, first, electrical contact surface; and
    an anisotropic conductor, which is arranged between said support and said semiconductor chip and produces an electrically conducting connection between said at least one, first, contact surface and said at least one, second, contact surface, and which has a traversing opening, which at least overlaps with the opening in said second surface, so that said media-sensitive region of said semiconductor opening is contactable through said opening with an analyte, wherein:

said anisotropic conductor seals the region outside of said opening against contamination with the analyte;
said anisotropic conductor is elastic;
said elastic anisotropic conductor comprises a silicone layer with embedded gold filaments, which extend perpendicular to the plane of the silicone layer; and said semiconductor chip is a pH sensor element or a redox sensor element.

6. The sensor arrangement as claimed in claim 5, wherein:
said semiconductor chip has an ion-sensitive region.

* * * * *